United States Patent [19]

Theeuwes

[11] 4,235,236
[45] Nov. 25, 1980

[54] DEVICE FOR DISPENSING DRUG BY COMBINED DIFFUSIONAL AND OSMOTIC OPERATIONS

[75] Inventor: Felix Theeuwes, Los Altos, Calif.

[73] Assignee: Alza Corporation, Palo Alto, Calif.

[21] Appl. No.: 11,121

[22] Filed: Feb. 12, 1979

[51] Int. Cl.$^3$ ............................................. A61M 7/00
[52] U.S. Cl. ................................................ 128/260
[58] Field of Search ............................. 128/222–223, 128/260, 271; 424/19, 22

[56] References Cited

U.S. PATENT DOCUMENTS

| | | | |
|---|---|---|---|
| 3,993,072 | 11/1976 | Zaffaroni | 128/260 |
| 4,060,084 | 11/1977 | Chandrasekaran et al. | 128/260 |
| 4,111,201 | 9/1978 | Theeuwes | 128/260 |
| 4,111,202 | 9/1978 | Theeuwes | 128/260 |
| 4,111,203 | 9/1978 | Theeuwes | 128/260 |
| 4,127,127 | 11/1978 | Wong et al. | 128/260 |

*Primary Examiner*—C. Fred Rosenbaum
*Attorney, Agent, or Firm*—Paul L. Sabatine; Edward L. Mandell; Thomas E. Ciotti

[57] ABSTRACT

A device is disclosed for delivering an agent to an environment of use at a substantially constant rate over time. The device comprises a wall formed of a microporous material surrounding a compartment housing the agent and a thermodynamic member. The member comprises a film formed of an expandable, semipermeable material surrounding a means for expanding the member. The member can occupy any space-position in the compartment, and it also can be in contact with the wall. In operation, when the device is in the environment, agent is delivered from the device by diffusion through fluid-filled paths in the microporous wall, with external fluid simultaneously entering the compartment through the paths, also, fluid is imbibed by the member from fluid present in the compartment or directly across the wall causing it to expand, fill the compartment and continuously maintain agent in a substantially saturated state at the wall, thereby delivering agent at a substantially zero order rate of release from the device over a prolonged period of time.

21 Claims, 5 Drawing Figures

DEVICE FOR DISPENSING DRUG BY COMBINED DIFFUSIONAL AND OSMOTIC OPERATIONS

FIELD OF THE INVENTION

This invention pertains to a diffusional device. More particularly, the invention relates to a diffusional device for delivering an useful agent at a substantially zero order rate of release over a prolonged and extended period of time. Specifically, the invention concerns a device that delivers a useful agent by a combination of diffusional and osmotic physical-chemical principles for effecting controlled delivery over time.

BACKGROUND OF THE INVENTION

Devices designed for delivering useful agents are becoming increasingly important articles of manufacture. The devices enjoy a wide application in commerce which includes the agriculture and pharmaceutical industries. Generally, the devices operate by diffusion, and they consists of an active agent housed within an inert wall structure. If, the thermodynamic activity of the agent is maintained substantially constant in the device, then a steady state will be established with the release rate of agent from the device substantially constant over time. This is commonly referred to as zero order release, a phrase suggested by physical-chemical kinetics.

If, however, the agent is present in the device in an undersaturated amount, of if the agent is present in a saturated amount with no excess agent phase, the thermodynamic activity and concomitantly the release rate will fall exponentially over time. This activity is commonly referred to as first order release, a phrase also suggested by physical-chemical kinetics. The zero order release is the most preferred of the two different rates of release for many applications, because in many applications the amount of agent consumed as a function of time is constant, requiring a constant, zero order rate of supply of agent in order to achieve and maintain a constant desired effect over time. It will be appreciated in view of this presentation, that if a device is provided that can exhibit a substantially zero order release over time, the device would have a positive commercial use and also represent a major contribution to delivery science.

OBJECT OF THE INVENTION

Accordingly, it is an immediate object of this invention to provide a device that has useful thermodynamic properties for delivering an agent over time.

Another object of the invention is to make available a device that has an internal space consuming member for providing a device that exhibits a more constant, predictable release rate profile of useful agent.

Yet another object of the invention is to make available a device having a constant activity source by providing a device having a wall and an internal expandable force that operates to maintain agent in the device in a concentrated state at the agent wall interface.

Still another object of the invention is to make available a device for delivering an agent whose release is controlled by Fickian diffusion through fluid-filled paths in a microporous wall with the agent activity at the internal boundary layer kept at a substantially saturated level during the agent release period.

Yet still another object of the invention is to make available a device that delivers an agent at a substantially constant rate by eliminating a receding boundary interface and its accompanying dramatic drop in diffusion delivery rate by providing a device that substantially maintains the agent at a saturated level at the boundary interface.

Other objects, features, aspects and advantages of the invention will be more apparent to those versed in the art from the following detailed specification, taken in conjunction with the figures and the accompanying claims.

SUMMARY OF THE INVENTION

This invention concerns a device for delivering a beneficial agent to an environment of use. The device consists essentially of a microporous wall surrounding a compartment containing agent and an expandable member. The member consists of an expandable semipermeable film surrounding a means for expanding the member, which means is selected from the group consisting of an osmotically effective solute, a gas generating couple and a swellable polymer. In operation, agent is released from the device by the combined physical-chemical actions of the device and the member, which actions embrace agent diffusing through fluid-filled paths in the microporous wall and the member expanding to continuously fill the compartment, whereby the combined actions causes the beneficial agent to be delivered from the device at a controlled and substantially zero-order rate of release over a prolonged period of time.

BRIEF DESCRIPTION OF THE DRAWINGS

In the drawings, which are not drawn to scale, but are set forth to illustrate various embodiments of the invention, the figures are as follows:

FIG. 2 is an opened view of the device of FIG. 1, which FIG. 2 illustrates the internal compartment and the thermodynamic member manufactured as an integrally formed device;

In the drawings and specification, like parts in related figures are identified by like numbers. The terms appearing earlier in the specification and in the description of the drawings, as well as embodiments thereof, are further detailed elsewhere in the disclosure.

DETAILED DESCRIPTION OF THE DRAWINGS

Figure 1:
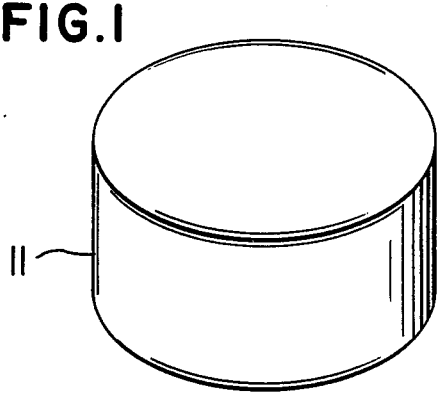
FIG. 1 is a view of a device designed and manufactured for orally administering a beneficial drug to a warm-blooded animal.

Turning now to the drawings, in detail, which are examples of various delivery devices of the invention, and which examples are not to be considered as limiting, one example of a device is indicated in FIG. 1 by the numeral 10. In FIG. 1, device 10 comprises a body 11 that can be shaped, sized, structured and adapted for easy placement and prolonged retention in an environment of use for the controlled, continuous delivery of a beneficial agent thereto.

Figure 2:
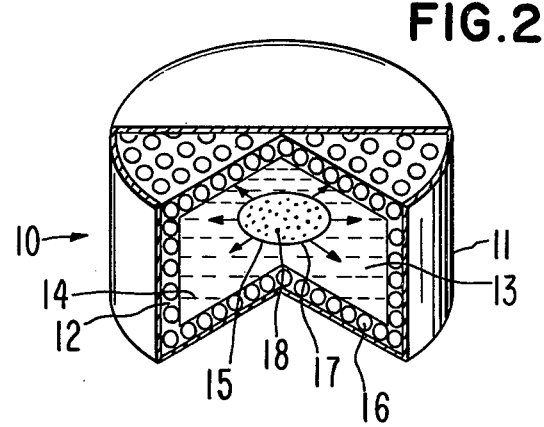

In FIG. 2, device 10 of FIG. 1 is seen in part opened-section, with its outer top layer partly sectioned-off, for elucidating the structure of device 10. In FIG. 2, device 10 comprises a body 11 having an exterior wall 12 that surrounds and forms a compartment 13. Compartment 13 contains an useful agent 14 and a thermodynamic member 15 that functions to maintain agent 14 in a substantially saturated state in compartment 13, especially during the time device 10 is in operation in a preselected environment of use. In FIG. 2, member 15 can, as in the embodiment shown, occupy a place near the center of compartment 13, or it can occupy any other place in compartment 13. Also, in an additional embodiment member 15 can be partially or have a large part of its surface in contact with the inside surface of wall 12.

Wall 12 of device 10 is formed of a microporous material consisting of a plurality of microscopic-sized interconnected pores or voids. The pores, illustrated as circles 16 for discussion herein, can be continuous with openings on both sides of wall 12, the pores can be interconnected through tortuous paths or regular and irregular shapes, including curved, curved-linear, randomly oriented continuous paths, hindered connected paths and pores, and other paths and pores discernible by microscopic examination. Generally, materials possessing from 5 to 95% pores and having a pore size of from 50 angstroms to 100 microns can be used for making wall 12. The pores and connecting intra-wall paths can be preformed in wall 12 with microporous wall 12 then manufactured into device 10. In a presently preferred embodiment, wall 12 contains a multiplicity of pore-formers, not shown, that are dessolved or leached from wall 12, which is integrally manufactured as device 10. In this embodiment, the pore-formers are removed when device 10 is in the environment of use thereby forming microporous wall 12 in the environment of use during operation of device 10.

The microporous paths of wall 12 are in one embodiment prefilled or they are filled in the environment of use with a diffusive medium permeable to the passage of agent 14. The medium is generally non-toxic and it does not adversely effect the device, the wall, the agent and the environment. In one embodiment, the medium is a liquid phase comprised of a solution, a colloidal solution or a sol, the medium can be polar, semi-polar or non-polar, or it can be a liquid present in the environment of use, including water, biological fluids, saline and buffers.

Thermodynamic member 15 in compartment 13 of device 10 consists essentially of a film 17 made of a semipermeable polymer that is essentially impermeable to the passage of solute, gas and compounds, and permeable to the passage of fluid present in compartment 13. Film 17 is flexible and elastic, or it contains a plasticizer that imparts flexibility and expandability to member 15. Film 17 surrounds a means 18 for expanding member 15, and it, does not contain any beneficial or useful agent, including drug. Member 15 can occupy any position in compartment 13, or member 15 can occupy a position in compartment 13 in contact with wall 12. In this latter position, semipermeable film 17 of member 15 is in contact with microporous wall 12, defining and forming thereby, the functional equivalent of a semipermeable microporous laminate. In one embodiment, means 18 is an osmotically effective solute that exhibits an osmotic pressure gradient across film 18 against fluid in compartment 13. In operation, solute means imbibes fluid into member 15 from fluid in compartment 13 or across the laminate thereby enlarging and expanding member 15 to continuously fill compartment 13. In another embodiment, means 18 is a gas generating couple. In operation, couple means 18 imbibes fluid into member 15, in the manner described, wetting the couple and causing it to react and generate gas that enlarges and expands member 18 unidirectional or multidirectional in compartment 13. In another embodiment, means 18 is a lightly cross-linked polymer. In operation, polymer means 18 absorbs fluid that enters member 15, or across the laminate, causing it to swell and expand member 15. In all of these embodiments, as member 15 expands and fills space in compartment 13 it correspondingly continuously reduces or decreases the amount of space available for agent 14. This continual decrease in space substantially maintains agent 14 in a substantially saturated phase as there is less space and fluid available to the agent. The formation and maintenance of the saturated phase presents agent 14 to wall 12 at substantially the same rate and amount throughout the release period, thereby effecting for device 10 a zero order release rate.

Figure 3:
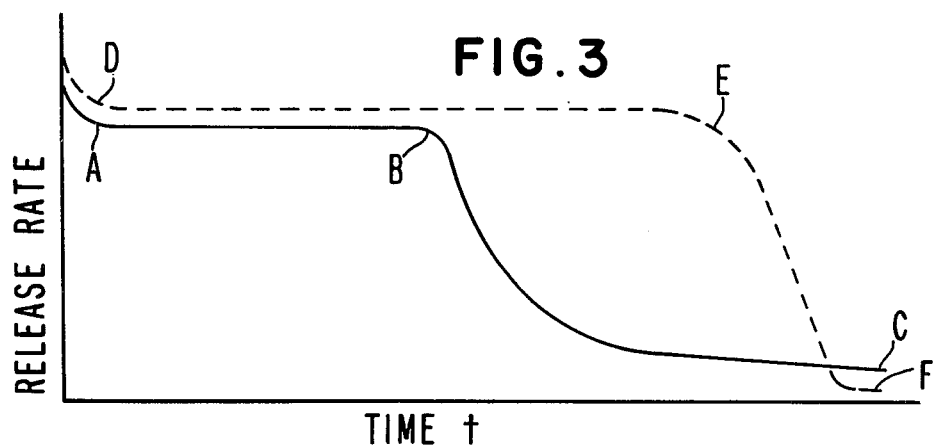
FIG. 3 is a graph that illustrates the improved delivery results obtained by the device of FIG. 1 and FIG. 2.

FIG. 3 illustrates the results obtained with devices made according to this invention. In FIG. 3, A–C represents the release rate profile for a device made without a means for presenting a constant, saturated amount of agent to a release rate controlling wall. For this condition, a steady-state exist from A to B with a rapid drop from B to C as the agent wall interface is depleeted of saturated agent. Also, in FIG. 3, D–F represents the release rate profile for a device made according to this invention having a means that concentrates that agent for presenting a constant, saturated amount of agent to the release rate controlling microporous wall. For this condition, a steady-state exists for the increased prolonged period of time from D to E with a decline from E to F as substantially all of the agent is released by the device. This latter device exhibits zero order release rate kinetics.

Figure 4:
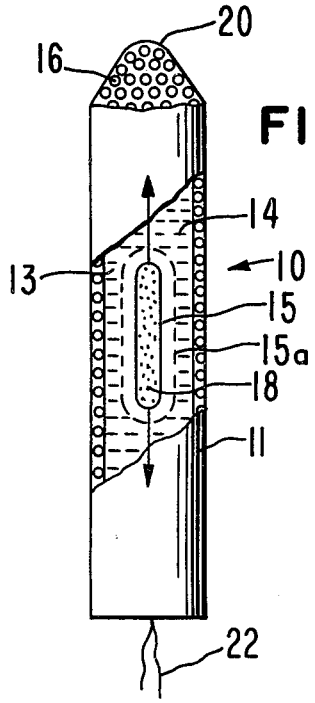
FIG. 4 illustrates a device provided by the invention and designed for dispensing a drug in a body passageway such as the vagina or the ano-rectal passageways; and, FIG. 5 is a side elevational view of an apparatus with portions broken away to illustrate one procedure that can be used for forming the walls and film of the devices provided by the invention.

FIG. 4 shows a device 10 designed, sized and styled for easy placement and comfortable retention in a body passageway, such as the vagina or the ano-rectal passageway. Device 10 has an elongated, cylindrical, self-sustaining shape with a pointed lead-end 20, a base-end 21, and it is equipped with a manually controlled cord 22 for easily removing device 10 from a body passage. Device 10 of FIG. 4 is structurally identical with device 10 of FIGS. 1, 2 and 3, as described above, and it operates in a like manner with member 15 expanding to 15a for continually occupying area in compartment 13. In an optional embodiment, not shown, member 15 can be in contact with wall 12, as described in FIG. 3. Device 10 of FIG. 4 in one embodiment contains a drug designed for release and absorption by the vaginal, or the rectal mucosa.

Figure 5:
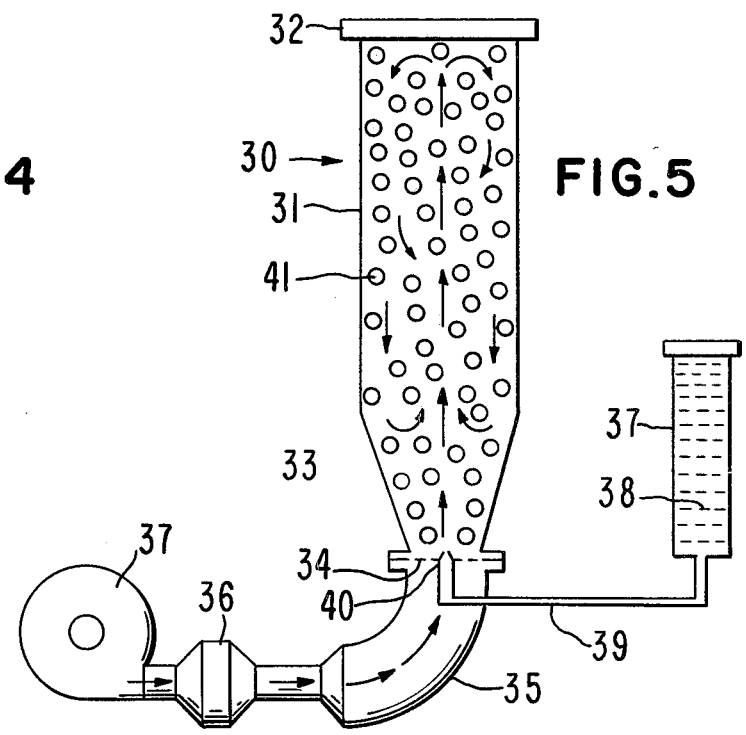

FIG. 5 illustrates an air-suspension apparatus 30 that can be used for carrying out the wall forming steps of the invention. In FIG. 5, apparatus 30 is composed of a cylindrical, columnar chamber 31 having an upper end 32 that can be opened for receiving materials. Chamber 31 has a conical section 33 at its lower end and that is equipped with a screen 34 for preventing materials from falling out of chamber 31.

Chamber 31 is joined to an enlarged elbow 35 that serves as an air duct attached to heater 36 and blower 37 for supplying heated air to chamber 31. A fluid supply chamber 37 containing wall forming material 38 is connected through supply line 39 to elbow 35. A needle valve assembly 40 feeds material 38 to chamber 31. In operation, with the blower and heater on, and chamber 31 filled with device intermediates 41, and wall forming material 38 being fed to chamber 31, a uniform wall pattern develops on intermediates 41. The intermediates move in chamber 31 in air flow patterns indicated by the arrows, leading to their conversion and the formation of device 10. Apparatus 30 also can be used in a like manner for manufacturing member 15.

While FIGS. 1 through 5 are illustrative of various devices that can be made according to the invention, it is to be understood those devices are not to be construed as limiting the invention, as the devices can take a wide variety of shapes, sizes and forms for delivering an agent including drugs to different environments of use. For example, the devices include buccal, implant, eye, artificial gland, cervical, intrauterine, ear, nose, dermal, subcutaneous, and blood delivery devices. The devices can be used in hospitals, veterinary clinics, nursing homes, sickrooms, and the like.

DETAILED DESCRIPTION OF THE INVENTION

In accordance with the practice of the invention it has now been found the diffusion delivery devices 10 can be manufactured with microporous wall forming polymers that are commercially available, or they can be made by art known methods. The microporous materials can be made and then manufactured into a device by etched nuclear tracking, by cooling a solution of flowable polymer below its freezing point whereby solvent evaporates from the solution in the form of crystals dispersed in the polymer, and then curing the polymer followed by removing the solvent crystals, by cold or hot stretching of a polymer at low or high temperatures until pores are formed, by leaching from a polymer soluble pore forming component by use of an appropriate solvent, and by dissolving or leaching a pore former from the wall of a device in operation in the environment of use. Processes for preparing miroporous materials are described in *Synthetic Polymer Membranes,* by R. E. Kesting, Chapters 4 and 5, 1971 published by McGraw Hill, Inc; *Chemical Reviews, Ultrafiltration,* Vol. 18, pages 373 to 455, 1934; *Polymer Eng. and Sci.,* Vol. 11, No. 4, pages 284 to 288, 1971; *J. Appl. Poly. Sci.,* Vol. 15, pages 811 to 829, 1971; and in U.S. Pat. Nos. 3,565,259; 3,615,024; 3,751,536; 3,801,692; 3,852,224; and 3,849,528.

Materials useful for making the microporous wall include polycarbonates comprised of linear polyesters of carbonic acid in which carbonate groups recur in the polymer chain, microporous materials prepared by the phosgenation of a dihydroxyl aromatic such as bisphenol a, microporous poly(vinylcholoride), microporous polyamides such as polyhexamethylene adipamide, microporous modacrylic copolymers including those formed from poly(vinylchloride) 60% and acrylonitrite, microporous styrene-acrylic and its copolymers, porous polysulfones characterized by diphenylene sulfone groups in a linear chain thereof, halogenated poly(vinylidene), polychloroethers, acetal polymers, polyesters prepared by esterification of a dicarboxylic acid or anhydride with an alkylene polyol, poly(alkylenesulfides), phenolic polyesters, microporous poly(saccharides), having substituted anhydroglucose units exhibiting a decrease permeability to the passage of water and biological fluids, asymmetric porous polymers, cross-linked olefin polymers, hydrophobic or hydrophilic microporous homopolymers, copolymers or interpolymers having a reduced bulk density, and materials described in U.S. Pat. Nos. 3,595,752; 3,643,178; 3,654,066; 3,709,774; 3,718,532; 3,803,061; 3,852,224; 3,852,388; and 3,853,601; in British Pat. No. 1,126,849; and in Chem. Abst., Vol. 71 427F, 22573F, 1969.

Additional microporous materials for forming wall 12 include poly(urethanes), cross-linked, chain-extended poly(urethanes), microporous poly(urethanes) in U.S. Pat. No. 3,524,753, poly(imides), poly(benzimidazoles), collodion, (cellulose nitrate with 11% nitrogen), regenerated proteins, semi-solid cross-linked poly(vinylpyrrolidone), microporous materials prepared by diffusion of multivalent cations into polyelectrolyte sols as in U.S. Pat. No. 3,565,259, anisotropic permeable microporous materials of ionically associated polyelectrolytes, porous polymers formed by the coprecipitation of a polycation and a polyanion as described in U.S. Pat. Nos. 3,276,589; 3,541,055; 3,541,006; and 3,546,142, microporous derivatives of poly(styrene) such as poly(sodium-styrene-sulfonate) and poly(vinyl benzyl-trimethyl-ammonium chloride), the microporous materials disclosed in U.S. Pat. No. 3,615,024 and U.S. Pat. Nos. 3,646,178 and 3,852,224.

The pore-formers useful for forming the microporous wall in the environment of use include solids and pore-forming liquids. The term pore-former as used herein also embraces micropath former, and removal of the pore and/or path former leads to both embodiments. In the expression pore-forming liquids, the term for this invention generically embraces semi-solids and viscous fluids. The pore-formers can be inorganic or organic and the wall forming polymer usually contains from 5 to 70% by weight of the pore-former, and more preferably about 20 to 50% by weight. The term pore-former for both solids and liquids include substances that can be dissolved, extracted or leached from the precursor microporous wall by fluid present in the environment of use to form operable, open-celled type microporous walls. Additionally, the pore-formers suitable for the invention include pore-formers that can be dissolved, leached, or extracted without causing physical or chemical changes in the polymer. The pore-forming solids have a size of about 0.1 to 200 microns and they include alkali metal salts such as lithuim carbonate, sodium chloride, sodium bromide, sodium carbonate, potassium chloride, potassium sulfate, potassium phosphate, sodium benzoate, sodium acetate, sodium citrate, potassium nitrite, and the like. The alkaline earth metal salts such as calcium phosphate, calcium nitrate, calcium chloride, and the like. The transition metal salts such as ferric chloride, ferrous sulfate, zinc sulfate, cupric chloride, manganese fluoride, manganese fluorosilicate, and the like. Organic compounds such as polysaccharides including the sugars sucrose, glucose, fructose, mannitol, mannose, galactose, aldohexose, altrose, talose, sorbitol and the like. They can be polymers soluble in the environment of use such as Carbowaxes ®, Carbopol ®,and the like. The pore-formers are non-toxic and on their removal from the wall, channels or paths are formed through the wall that fills with fluid present in the environment. The paths become a means, or diffusional path for diffusion of agent, or drug from the device. The pores extend from inside wall 12 to the outside of wall 12 for effective release of agent or drug to the exterior of device 10.

The selective permeable materials used for forming film 17 of member 15 include polymers permeable to fluid present in compartment 13 while remaining impermeable to solutes, agents and drugs. Typical material include semipermeable polymers, also known to the art as osmosis membranes. The semipermeable polymers include cellulose acylate, cellulose diacylate, cellulose triacylate, cellulose ethers and cellulose esters. Typical semipermeable polymers include cellulose acetate, cellulose diacetate, cellulose triacetate, dimethyl cellulose acetate, cellulose acetate ethyl carbamate, and the like. Other semipermeable polymers include polyurethane, and selectively semipermeable polymers formed by the coprecipitation of a polyanions and a polycation. Generally, semipermeable polymers useful for forming wall 12 will have a fluid permeability of $10^{-5}$ to $10^{-1}$ (cc.mil/cm$^2$hr.atm) expressed per atmosphere of hydrostatic or osmotic pressure difference across film 17 at the temperature of use.

The osmotically effective compound that can be used in member 15 includes organic and inorganic compounds or solutes that exhibit an osmotic pressure gradient across semipermeable film 17 against fluid in compartment 13. Osmotically effective compounds useful for this purpose include magnesium sulfate, magnesium chloride, sodium chloride, lithium chloride, potassium sulfate, sodium carbonate, potassium acid phosphate, mannitol, urea, sucrose, and the like. The osmotically effective compounds are also known as osmagents and they are disclosed in U.S. Pat. Nos. 3,854,770 and 4,077,407. These patents are assigned to the Alza Corporation of Palo Alto, California.

The swellable polymers that can be used in expansion member 15 for expanding and enlarging member 15 include lightly cross-linked hydrophilic polymers. These polymers swell in the presence of fluid to a high degree without dissolution, usually exhibiting a 5 to 50 fold volume increase. Exemplary hydrogels include poly(hydroxyalkyl methacrylates), poly(acrylamide), poly(methacrylamide), poly(N-vinyl-2-pyrrolidone), anionic and cationic hydrogels, polyelectrolyte complexes, a water-insoluble, water-swellable copolymer produced by forming a dispersion of finely divided copolymers of maleic anhydride with styrene, ethylene, propylene butylene or isobutylene cross-linked with from about 0.001 to about 0.5 moles of a polyunsaturated cross-linking agent per mole of maleic anhydride in the copolymer as disclosed in U.S. Pat. No. 3,989,586, the water-swellable polymers or N-vinyl lactams as disclosed in U.S. Pat. No. 3,992,652, semi-solid cross-linked poly(vinyl pyrrolidone), diester cross-linked polyglucan hydrogels as described in U.S. Pat. No. 4,002,173, the anionic hydrogels of heterocyclic N-vinyl monomers as disclosed in U.S. Pat. No. 4,036,788, the ionogenic hydrophilic gels as described in *J. Biomedical Mater, Res.*, Vol. 7, pages 123 to 126, 1973, and the like.

The gas generating means for use in member 15 include an effervescent couple having one solid acid compound and one basic compound that dissolve and react in the presence of fluid in member 15 to produce carbon dioxide that expands member 15. The acid include organic acids such as malic, fumaric, tartaric, itaconic, maleic, citric, adipic, succinic and mesaconic, and inorganic acids such as sulfamic or phosphoric, also acid salts such as monosodium citrate, potassium acid tartrate and potassium bitartrate. The basic compounds include metal carbonates and bicarbonates salts, such as alkali metal carbonates and bicarbonates. Exemplary materials include lithium, sodium, and potassium carbonates and bicarbonates, and the alkaline earth compounds magnesium and calcium carbonates and bicarbonates. The essentially anhydrous or dry couple is preferred, preferably in substantially stoichiometrically balance to produce a combination that generates carbon dioxide. The acid and base materials can be used in any convenient proportion between 1 to 200 parts to 1 parts on a weight basis to produce the desired results.

Exemplary plasticizers suitable for adding to film 17 or member 15 to impart flexibility and stretchability include cyclic and acyclic plasticizers. Typical plasticizers are those selected from the group consisting of phthalates, phosphates, citrates, adipates, tartrates, sebacates, succinates, glycolates, glycerolates, benzoates, myristates, sulfonamides halogenated phenyls, poly(alkylene glycols), poly(alkylenediols), polyesters of alkylene glycols, and the like.

Exemplary plasticizers further include dialkyl phthalates, dicycloalkyl phthalates, diaryl phthalates and mixed alkyl-aryl phthalates as represented by dimethyl phthalate, dipropyl phthalate, di(2-ethylhexyl)phthalate, di-isopropyl phthalate, diamyl phthalate and dicapryl phthalate; alkyl and aryl phosphates such as tributyl phosphate, trioctyl phosphate, tricresyl phosphate, trioctyl phosphate, tricresyl phosphate and triphenyl phosphate; alkyl citrate and citrates esters such as tributyl citrate, triethyl citrate, and acetyl triethyl citrate; alkyl adipates such as dioctyl adipate, diethyl adipate and di(2-methoxyethyl)adipate; dialkyl tartrates such as diethyl tartrates and dibutyl tartrate; alkyl sebacates such as diethyl sebacate, dipropyl sebacate and dinonyl sebacate; alkyl succinates such as diethyl succinate and dibutyl succinate; alkyl glycolates, alkyl glycerolates, glycol esters and glycerol esters such as glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate and triethylene glycol dipropionate. Other plasticizers include camphor, N-ethyl (o- and p-toulene) sulfonamide, chlorinated biphenyl, benzophenone, N-cyclohexyl-p-toluene sulfonamide, and substituted epoxides.

Suitable plasticizers can be selected for blending with film 17 forming materials by selecting plasticizers that have a high degree of solvent power for the materials, are compatible with the materials over both the processing and use temperature range, exhibit permanence as seen by a strong tendency to remain in the plasticized film and imparts flexibility to the film. Procedures for selecting a plasticizer having the described characteristics are disclosed in the *Encyclopedia of Polymer Science and Technology*, Vol. 10, pages 228 to 306, 1979, published by John Wiley & Sons, Inc., New York. Also, a detailed description pertaining to the measurement of plasticizer properties, including solvent parameters and compatibility, the Hildebrand solubility parameter, the Flory-Huggins interaction parameter, and the cohesive-energy density, CDE, parameter is disclosed in *Plasticization and Plasticizer Processes, Advances in Chemistry Series* 48, Chapter 1, pages 1 to 26, 1965, published by the American Chemical Society, Washington, D.C. The amount of plasticizer added generally is an amount sufficient to produce the desired film and it will vary according to the plasticizer and the materials. Usually about 0.1 part up to 20 parts, or higher, of the plasticizer can be used for 100 parts of film forming material with a presently preferred range of 1 part to 15 parts of plasticizer, or mixtures thereof for 100 parts of film forming materials.

The expressions "active agent" and "beneficial agent" as used herein broadly include any compound, composition of matter, or mixture thereof, that can be delivered from system 10 to produce a beneficial and useful result. The agents include air purifiers, algicides, antioxidants, biocides, catalysts, chemical reactants, cosmetics, contraceptives, drugs, disinfectants, food supplements, fermentation agents, fertility inhibitors, fertility promoters, fungicides, germicides, herbicides, insecticides, micro-organism attenuators, pheremones, pro-drugs, plant growth inhibitors, pesticides, preservatives, rodenticides, sex steriliants, slimicides, vitamins, and other agents that benefit the environment of use and animals. The term animals as used herein includes primates, mammals, warm-blooded animals, humans and other animals. The devices also can be used for dispensing drug to reptiles, avians and pisces.

Representatives of drugs that can be delivered by device 10 include tranquilizers such as reserpine, thiopropazate, perphenazine and chloropromazine; psychic energizers such as amitripyline, imipramine and methylphenidate; analgesics-antipyretics such as aspirin, phenacetin and salicylamide; anti-inflammatories such as hydrocortisone, dexamethazone, prednisolone, and phenylbutazone; decongestants such as phenylephrine and pseudoephedrine; and other therapeutic agents.

Representative of typical drugs that can be dispensed in the vagina from device sized, shaped and adapted for easy insertion and comfortable retention in the vagina include allantorn, aminoacridine hydrochloride, benzocaine, benzalkonium chloride, candicidin, dienestrol, dibucaine, ephedrine sulfate, furazolidone, gentain violet hydrocortisone, methylbenzethium chloride, phenylmercuric acetate, providone-iodine, sulfanilamide, sulfisoxazole, tetracaine, undecylenate, and the like. These drugs and their present dose are known to the art. See *Techniques of Medication,* by Eric W. Martin, pages 106 to 107, 1969, published by J. B. Lippincott Company, Philadelphia.

Representative of drugs that can be dispensed in the ano-rectal environment from a device shaped, sized and adapted for easy insertion and comfortable retention therein include acetarsol, adrenaline with benzocaine, aminophylline, aminophylline with pentobarbital sodium, ampicillin, aspirin, astroscopolamine, belladonna, benzocaine, bisacodyl, bismuth subgallate, caffeine, ergotamine tartrate, chloralhydrate, chlorpromazine, cinchocaine, cyclomethycaine sulfate, dimenhydrinate, hydrocortisone, ichthammol, isoprenaline, metronidazole, morphine, oxymorphine hydrodiamine, thiethylperazine meleate, and the like. These drugs and their present dose are known to the medical art. See *Martindale The Extra Pharmacopolia,* Edited by Ainley Wade, *General Index,* page 2056, 1977, published by the Pharmaceutical Press, London; and, *National Drug Code Directory, published by Public Health Service U.S. Department of Health, Education and Welfare, Washington.*

The drug present in the compartment of the device can be in various forms, such as uncharged molecules, molecular complexes, pro-drug, pharmacologically acceptable salts such as hydrochlorides, hydrobromides, sulfate, laurylate, palmitate, phosphate, nitrate, borate, acetate, maleate, tartrate, oleate, and salicylate. For acidic drugs, salts of metals, amines, or organic cations, for example quaternary ammonium salts can be used. Derivatives of drugs such as esters, ethers and amides, which have solubility characteristics suitable for use herein can be used. The agent or drug can be in the compartment as a suspension, dispersion, paste, cream, particle, granule, emulsion, solution, powder, and the like.

The amount of agent in device 10 is preferably initially in excess of the amount that can be dissolved in fluid that enters compartment 13. Under this physical state, when agent 14 is in excess, device 10 will diffusingly operate to give a substantially constant rate of release over time, then member 15 activates and the combined action of member 15 and device 10 operating as a unit device produces a substantially constant rate of release over a prolonged period of time. The rate of agent release can also be varied by having different amounts of agent in the compartment to form solutions containing different concentrations of agent for delivery from the device 10. Generally, device 10 can house from 0.01 ng to 7 g or more, with individual devices controlling for example, 25 ng, 1 mg, 5 mg, 125 mg, 250 mg, 500 mg, 1 g, 1.5 g, 7.5 g, 10 g, and the like.

The devices of the invention are manufactured by standard techniques. For example, in one embodiment, first a delivery member is made by surrounding an osmotic agent, gas generating couple, or swellable polymer with a semipermeable film, and then the agent and member, and other ingredients that may be housed in the compartment and a solvent are mixed into a solid, semi-solid or gel by conventional methods such as ball-milling, calendering, stirring or rollmilling and then pressed into a preselected shape. The wall forming the system can be applied by molding, spraying or dipping the pressed shape into wall forming materials. In another embodiment, a wall can be cast, shaped to the desired dimensions to define a wall that surrounds a compartment that is filled with agent and means, and then closed. Walls forming the system also can be joined by various joining techniques such as high frequency electronic sealing that provides clean edges and firmly formed walls. Another, and presently preferred technique that can be used in the air suspension procedure previously described. Air suspension procedures are described in U.S. Pat. No. 2,799,241; in *J. Am. Pharm. Assoc.,* Vol. 48, pages 451 to 459, 1959; and ibid., Vol. 49, pages 82 to 84, 1960. Other wall forming and film forming techniques such as pan coating can be used in which the materials are deposited by successive layering of the polymer solution on the agent and the member tumbling in a rotating pan. Other standard manufacturing procedures are described in *Modern Plastics Encyclopedia,* Vol. 46, pages 62 to 70, 1969; and in *Pharmaceutical Sciences,* by Remington, 14 Ed., pages 1626 to 1678, 1970, published by Mack Publishing Company, Easton, Penna.

Exemplary solvents suitable for manufacturing the wall, or the film include inert inorganic and organic solvents that do not adversely harm the wall forming materials, the film forming materials, and the final device. The solvents broadly include members selected from the group consisting of aqueous solvents, and organic solvents, such as alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl, acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol.

The following example is merely illustrative of the present invention and should not be considered as limiting the scope of the invention in any way, as this example and other equivalents thereof will become apparent to those versed in the art in the light of the present disclosure, the drawings and the accompanying claims.

EXAMPLE 1

First, an expandable member is manufactured by compressing 125 mg of sodium chloride and then coating the pressed osmagent in an air suspension machine with a film forming composition comprising 70% cellulose acetate having an acetyl content of 32% mixed with 30% polyethylene glycol having a molecular weight of 400, dissolved in methylene chloride-methanol, 80:20, until an expandable film is formed on the member.

Next 235 mgs of dry, procainamide is mixed with the member, the mixture compressed and placed in an air suspension machine. The microporous wall is formed from a composition consisting of 65 g of cellulose acetate having an acetyl content of 32%, 41 g of the micropore-former hexanehexol, 11.7 g of polyethylene glycol 400, and a wall forming solvent consisting of 1900 ml of acetone and 375 ml of water. The wall is formed by air tumbling until about a 7 mil thick microporous pore-forming wall is applied on the device.

EXAMPLE 2

A device is made as follows: first, an expandable member is made by pressing a mixture of 56.7% potassium hydrogen carbonate, 40.2% citric acid and 3% anhydrous magnesium silicate, and the gas generating means placed in an air suspension machine. The gas generator is surrounded with a film consisting of 90% cellulose acetate having an acetyl content of 32% having homogenously dispersed therein 10% by weight of polyethylene glycol having a molecular weight of 400. The film forming process is carried out with a solvent consisting of methylene chloride-methanol, 80:20, volume: volume, to yield the expandable member.

Next, the member is surrounded by 500 mg of potassium chloride, by compression in a Manesty machine, and a microporous wall is deposited around the member-drug unit. A microporous wall of poly(vinyl chloride) with continuous diffusional paths is prepared by leaching a sheet of polymer consisting the poly(vinyl chloride) containing the pore forming agent poly [p-dimethyl-amino-styrene]. The wall is formed by casting in a joint solvent cyclohexane and the solvent evaporated. Then, an aqueous acidic solution of hydrochloric acid is used to leach the pore formers and yield the microporous wall. The leaching is carried out at room temperature followed by washing with distilled water to remove the acid. The microporous wall is applied to fully surround the member drug loaded device.

EXAMPLE 3

A therapeutic device is manufactured in the form of an oral device for delivering procainamide hydrochloride to the gastrointestinal tract of a warm-blooded animal as follows: first, 200 mg of lightly cross-linked, swellable poly(hydroxyalkyl) methacrylate is coated with a film in an air suspension machine with a composition comprising 70% cellulose acetate having an acetyl content of 32% mixed with 30% of polyethylene glycol having a molecular weight of 400 dissolved in methylene chloride methanol, 80:20, until the polymer is encapsulated with a semipermeable film 17 to yield member 15. Next, 235 mg of procainamide hydrochloride is pressed into a solid mass having a shape corresponding to the shape of member 15 and joined thereto by spreading a drop of liquified cellulose acetate between their interfaces. Then, the just-formed member-drug composite is surrounded with a wall of microporous polymeric polypropylene having a void volume of 0.565 to 0.075 cm.$^3$/gm., a density of 0.60 to 0.85 gm./cm$^3$., and a pore size of 150 to 5000 angstroms, as disclosed in U.S. Pat. No. 3,426,754, to yield device 10.

The novel devices of this invention uses an expandable member for the obtainment of precise diffusional release rates and enhanced delivery of agent to environments of use while simultaneously maintaining the integrity and character of the device. And, while there has been described and pointed out features of the invention as applied to presently preferred embodiments, those skilled in the art will appreciate that various modifications, changes, additions and omissions in the device illustrated and described that can be made without departing from the spirit of the invention.

I claim:

1. A device for the controlled delivery of a beneficial agent to an environment of use, said device comprising:
   (a) a microporous wall having a plurality of micropaths through the wall, said microporous wall surrounding and defining:
   (b) a compartment;
   (c) a beneficial agent in the compartment; and,
   (d) an expandable member in the compartment, said member comprising a flexible, semipermeable film surrounding an osmotically effective solute, a gas generating couple, or a swellable polymer; and,
   (e) wherein, when the device is in operation in the environment of use, the device continuously delivers agent by combined diffusional and osmotic operations, to the environment of use over a prolonged period of time.

2. The device for the controlled delivery of a beneficial agent according to claim 1 wherein the micropaths in the wall are formed in the environment of use.

3. The device for the controlled delivery of a beneficial agent according to claim 1 wherein the agent is a drug selected from the group consisting of local and systemic acting drugs.

4. The device for the controlled delivery of a beneficial agent according to claim 1 wherein when the device is in the environment of use the micropaths fill with fluid present in the environment.

5. The device for the controlled delivery of the beneficial agent according to claim 4, wherein in operation, agent is delivered from the device by diffusion through the micropaths in the microporous wall, with the member in the compartment absorbing fluid from the compartment, expanding and continuously filling the compartment for substantially maintaining the concentration of agent in a saturated phase at the microporous wall, thereby delivering agent at a zero-order rate of release over a prolonged period of time.

6. A device for the controlled delivery of the beneficial agent according to claim 1 wherein the semipermeable film is made of a member selected from the group consisting essentially of a cellulose ester, cellulose ether, cellulose acylate, cellulose diacylate, and cellulose triacylate.

7. The device for the controlled delivery of the beneficial agent according to claim 1 wherein the agent is a drug and the device is sized, shaped, and adapted for orally administering the drug to the gastrointestinal tract.

8. The device for the controlled delivery of the beneficial agent according to claim 1 wherein the agent is a drug, and the device sized, shaped and structured for administering drug to a body passageway.

9. The device for the controlled delivery of the beneficial agent according to claim 1 wherein the swellable polymer is cross-linked and is a member selected from the group consisting of poly(hydroxylalkyl methacrylate), poly(acrylamide), poly(N-vinyl-2-pyrrolidone), anionic hydrogels and cationic hydrogels.

10. The device for the controlled delivery of the beneficial agent according to claim 1 wherein the gas generating couple comprises an acid selected from the group consisting of malic, fumaric, tartaric, itaconic, citric, succinic, adipic and mesaconic, and a basic compound selected from the group consisting of lithium carbonate, sodium carbonate, potassium carbonate, lithium bicarbonate, potassium bicarbonate, sodium bicarbonate, and magnesium bicarbonate.

11. The device for the controlled delivery of the beneficial agent according to claim 1 wherein the semipermeable film contains a plasticizer.

12. The device for the controlled delivery of the beneficial agent according to claim 1 wherein the microporous wall is from a microporous polymer selected from the group consisting of poly(urethane), poly(imides), poly(benzimidazoles), cross-linked poly(vinylpyrrolidone), poly(amides), poly(sulfones), poly(saccharides) and poly(saccharides having substituted anhydroglucose units.

13. The device for the controlled delivery of the beneficial agent according to claim 1 wherein the micropaths in the wall are formed by removing a pore-former having a size of about 0.1 to 200 microns.

14. The device for the controlled delivery of the beneficial agent according to claim 1 wherien the micropaths in the wall are formed by removing a member selected from the group consisting of an alkali metal salt and an alkaline earth metal salt, a carbohydrate, a polymer, and mixtures thereof.

15. The device for the controlled delivery of the beneficial agent according to claim 1, wherein the agent is a drug, the environment is the ano-rectal passageway, and the device is sized, shaped and designed for delivering the drug to said environment.

16. The device for the controlled delivery of the beneficial agent according to claim 1 wherein the member imbibs fluid present in the compartment.

17. The device for the controlled delivery of the beneficial agent according to claim 1 wherein the member imbibs fluid across the wall from the environment of use.

18. A method for the controlled administration of a beneficial drug to the anto-rectal passageway, which method comprises:
A. inserting into the ano-rectal passageway a device that releases drug by a combination of diffusional and osmotic operations, wherein the device comprises:
(1) a microporous wall having a plurality of micropaths through the wall, which microporous wall surrounds and defines;
(2) a compartment;
(3) a beneficial drug in the compartment; and,
(4) an expandable member in the compartment, said member comprising a flexible, semipermeable film surrounding an osmotically effective solute, a gas generating couple, or a swellable polymer;
B. admitting fluid from the ano-rectal passageway through the microporous wall into the compartment to form a solution containing drug, and for activating the member to osmotically imbibe fluid from within the compartment, increase in volume and supply the solution to the microporous wall; thereby,
C. delivering drug through the microporous wall by the combined operations to the ano-retal passageway over a prolonged period of time.

19. The method for the controlled administration of a beneficial drug to the ano-rectal passageway according to claim 18 wherein the drug housed in the compartment is a member selected from the group consisting of acetarsol, adrenaline with benzocain, aminophylline, aminophylline with pentobarbital sodium, ampicillin, aspirin, benzocaine, biscodyl, bismuth subgallate, ergotamine tartrate, chloropromazine, isoprenaline, metronidazole, and thiethylperazine.

20. A method for the controlled administration of a beneficial drug to the vagina, which method comprises:
A. inserting into the vagina a device that release drug by a combination of diffusional and osmotic operations, wherein the device comprises:
(1) a microporous wall having a plurality of micropaths through the wall, which microporous wall surrounds and defines;
(2) a compartment;
(3) a beneficial drug in the compartment; and,
(4) an expandable member in the compartment, said member comprising a flexible, semipermeable film surrounding an osmotically effective solute, a gas generating couple, or a swellable polymer;
B. admitting fluid from the vagina through the microporous wall into the compartment to form a solution containing drug, and for activating the member to osmotically imbibe fluid from within the compartment, increase in volume and supply solution to the microporous wall; thereby,
C. delivering drug through the microporous wall by the combined operations to the vagina over a prolonged period of time.

21. The method for the controlled administration of a beneficial drug to the vagina according to claim 20 wherein the drug housed in the vagina is a member selected from the group consisting essentially of allantorn, amenoarridine hydrochloride, benzocaine, benzalkonium chloride, candicidin, dienestrol, dibucaine, ephedrine sulfate, furazolidone, gentain violet, hydrocortisone, methylbenzethium chloride, phenylmercuric acetate, providone-iodine, sulfanilamide, sulfisoxazole, tetracaine, and undecylenates.

* * * * *